United States Patent [19]
Muller

[11] Patent Number: 5,208,698
[45] Date of Patent: May 4, 1993

[54] OPTICALLY-NEUTRAL LASER SHIELD

[75] Inventor: Richard A. Muller, Berkeley, Calif.

[73] Assignee: The Mitre Corporation, Bedford, Mass.

[21] Appl. No.: 630,156

[22] Filed: Dec. 19, 1990

[51] Int. Cl.$^5$ .................. G02B 26/08; G02B 3/00; G02B 5/22; G02F 1/03

[52] U.S. Cl. .................... 359/299; 359/302; 359/723; 359/890; 359/241; 351/44

[58] Field of Search .............. 350/354, 448; 359/241, 359/299, 302, 723, 890

[56] References Cited

U.S. PATENT DOCUMENTS

| | | | |
|---|---|---|---|
| 3,620,597 | 11/1971 | Schwartz et al. | 350/448 |
| 4,846,561 | 7/1989 | Soileau, Jr. et al. | 359/241 |
| 4,909,609 | 3/1990 | McDowell | 350/354 |

*Primary Examiner*—Rolf Hille
*Assistant Examiner*—Robert Limanek
*Attorney, Agent, or Firm*—Wolf, Greenfield & Sacks

[57] ABSTRACT

An optical device that is optically neutral to normal light but absorbs highly collimated light is formed as a mosaic of optical cells. Each cell has at least two refracting surfaces and a non linear material at a focus internal to those surfaces. In one form, the cell comprises two pairs of lenses with a layer of non-linear light absorbent material interposed between the lenses of each pair. The lens elements can be one-power telescopes. A first lens element focuses highly collimated light at its entrance aperture on the non-linear layer. The intensity of the focused light causes the non-linear layer to become opaque or reflective and thereby reduce, or substantially block, the transmission of highly collimated light. The second pair of lenses inverts the re-collimated light exiting the first lens pair. By arranging the optical cells in an array, it is possible to obtain a coherence of the light diffracted from individual cells to produce a wave front from the mosaic as a whole having a resolution that is superior to that of the cells.

10 Claims, 2 Drawing Sheets

OPTICALLY-NEUTRAL LASER SHIELD

BACKGROUND OF THE INVENTION

This invention relates in general to optical apparatus. More specifically, it relates to an optical structure which is neutral to normal light, but which blocks, or substantially reduces, the transmission of highly collimated light.

There is a long recognized need for a material, device, or system which will pass ordinary light with little or no adverse affect on the quality of the viewed image, but which will block, or at least reduce substantially, the transmission of highly collimated light, as from a laser. The invention is needed because the human eye and other optical devices such as cameras focus laser light to a small point thereby increasing the intensity of the light. Focusing optics are therefore their own worst enemy when subjected to laser light. Heretofore the principal solution to this problem has been to screen out radiation at the anticipated wavelength of the laser light, but to pass other wavelengths. To date, there are no laser shields known to applicant which are neutral to ordinary light and which reliably block laser light of any wavelength. In particular, there are no known laser shields which have these characteristics which are also readily formed into lenses for eyewear, windshields, windows and the like.

It is therefore a principal object of the present invention to provide a laser shield which is optically neutral to ordinary light, but which attenuates or blocks laser light.

A further object is to provide a laser shield with the foregoing advantages which operates independently of the wavelength of the laser light.

Another object of the present invention is to provide a laser shield that can be formed into a sheet of material that is substantially transparent to ordinary light and which can be formed into a wide variety of optical elements, such as eyewear, windshields and view ports.

A further object is to provide a laser shield in the form of a sheet material which can have a flat or curved geometry.

Another principal object of the invention is to form an extended, sheet-like laser shield having a resolution superior to the resolution of the component optical cells forming the sheet.

A further object is to provide a laser shield with the foregoing advantages which can be manufactured using conventional techniques and standard materials.

Still another object is to provide a laser shield which is comparatively thin, lightweight, and durable under normal use conditions.

Yet another object is to provide a laser shield with the foregoing advantages which ca be constructed to have acceptably low chromatic and spherical aberrations.

SUMMARY OF THE INVENTION

An array of optical cells extends transversely between a field of view and an imaging device, such as the human eye to form a shield. The cells are secured adjacent to one another adjacent lens elements preferably being formed from an integral piece of transparent material. The array or shield can be planar or curved to form glasses, windshields, windows or the like.

Each cell has the ability to focus collimated light incident on its entrance aperture to one focal point lying in a focal plane within the cell; it does not so focus uncollimated light to a single point. Each cell has a layer of material at this internal focal plane which attenuates or reflects light which is brought to a focus at this plane. Each cell also has the ability to re-collimate the light which has been so focused and so attenuated or reflected. The image incident on the entrance aperture is thereby reduced in intensity to a level that it will not damage the eye or other imaging device. Each cell also re-inverts the image so focused. Broad stated, each cell has at least two refracting surfaces that 1) brings incident collimated light to at least one internal focus, 2) provides a non linear material at this at least one internal focus, and 3) inverts the image so that collimated light exiting the cell is parallel to the light entering it.

In one form the attenuating or reflective layer is a layer of a non-linear material that is heated by the focused light and in response thereto becomes opaque or reflective to limit, and usually substantially block the transmission of collimated light through the cell. A suitable material is vanadium oxide. One arrangement for the focusing and re-collimating steps are lenses, whether single or multiple, thin or thick, spherical or a spherical. Focusing optical fibers may also be used. In one form, the lens elements are paired thick lenses that together form a one power telescope with the focal plane at the internal surfaces of the paired lenses. The second pair of such lenses inverts the image. The total thickness of this four element array, including the non linear layer, is about four times the focal length of the lens.

The array is formed with precision so that the light exiting each cell of the array combines coherently to produce an image with a resolution greater than that obtainable with a single one of the optical cells. Preferably the cells are located with precision within one quarter of the wavelength of the light being transmitted through the device. Also, to provide an enhanced field of view, the lens elements of the cells can be optically coupled to one another and the lens elements within a cell can have slightly different indices of refraction to achromatize the array.

In a two lens element form having four refracting surfaces, the lens can be thick with each lens having a thickness equal to twice its focal length and with the non-linear material inserted inside. In another two lens form, one lens is thin and focuses the incident light on the non-linear material. The second lens is thick and inverts the light. In a three lens form, a first lens, preferably thin, focuses the light on the layer of non linear material and a pair of mutually spaced thin lenses on the opposite side of the non linear layer invert the image. Additional lenses can be added to reduce aberrations.

These and other features and objects of the invention will be more fully understood from the following detailed description which should be read in light of the accompanying drawings.

DETAILED DESCRIPTION OF THE PREFERRED EMBODIMENTS

Figure 1:
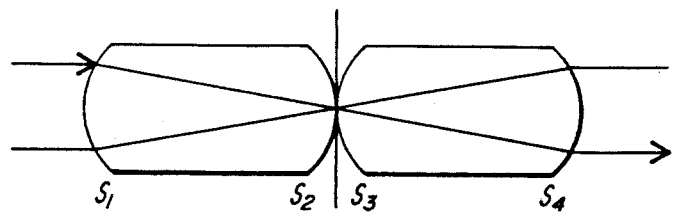
FIG. 1 is a schematic view in cross section of a one power telescope and associated non-linear layer forming a component of the laser shield of the present invention.

Turning first to the ray directing components of the present invention, FIG. 1 shows an inverting one power telescope 12 which forms an optical cell of an extended array 14 or mosaic or such cells that together comprise an optically-neutral shield against collimated light, particularly laser light. The light originates in a field of view 16 and exits the cell to an imaging device 18 such as a human eye, a photodetector or a camera. As shown in FIG. 1, two parallel collimated rays A and B enter a first lens element 20 of the cell at surface $S_1$ which is curved at a radius r to bring the rays to a focus at a focal plane 22 at the interface between an exit surface $S_2$ of lens 20 and an entrance surface $S_3$ of lens 24 which together act as a field lens by imaging the entrance aperture $S_1$ on the exit aperture defined by surface $S_4$. These surfaces give the telescope a wide field of view. (If the field of view is sufficiently narrow, such a field lens is not necessary.) The lens elements can be made of glass or plastic. The curvatures illustrated are roughly correct for parallel rays A and B where the index of refraction of the lenses 20,24 is 1.5. The materials of the lenses can have slightly different indices to achromatize the combination. The lenses are thick lenses to make their miniaturization easier, but there is no reason why thin lenses could not be used for one or both of the lenses. The final surface $S_4$ images the focal plane on to infinity with the image inverted.

The focal length of each element could be, for example, twice the diameter of the lens. Its "F number", $F=f/D$, is therefore 2. The lens markers formula gives the radius of curvature of a single surface as:

$$r = \frac{n-1}{n} f \approx \frac{f}{3} = \frac{2}{3} D.$$

where n is the index of refraction of the lens material, f is the focal length of the lens, and D is its diameter. The total thickness of this lens pair is 2f.

Figure 2:
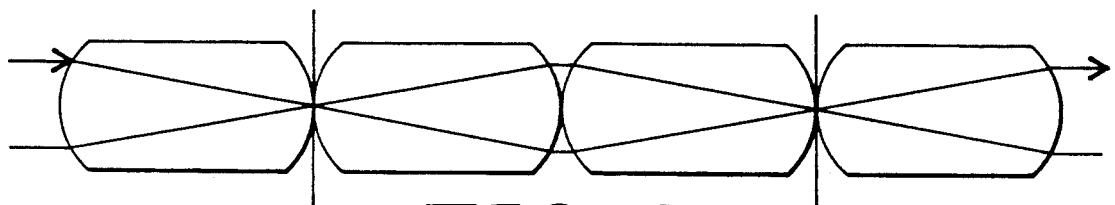
FIG. 2 is a view corresponding to FIG. 1 of an alternate embodiment of the invention shown in FIG. 1 using four thick lens elements.

While there are many ways to invert the image exiting the surface $S_4$, a simple way is shown in FIG. 2 where two inverting telescopes of the type shown in FIG. 1 are placed along the same optical axis, like parts being identified with the same reference numbers. As shown in FIG. 2, the rays A and B exiting the surface $S_4$ of the righthand telescope 12' are inverted to the original orientation of ray had on entering the surface $S_1$ of the first or lefthand telescope 12. The thickness of this four element cell defined by telescopes 12,12' is $4f=4DF$. Thus for light entering the telescope, the image one sees at the exit aperture is almost the same as one would see if the telescope were not present, except that the image viewed appears closer by the thickness of the telescope, 4DF. The telescope is therefore optically neutral. For the present purpose we are interested in having a shielding gain when the telescope transmits collimated light. We define the collimated light gain of the system, G, to be the ratio of the intensity of the light in the focal plane to the intensity at the aperture. The linear size of the image at the focal plane is $\lambda f/D$, where $\lambda$ is the wavelength of the incident light, so $G=(D^2/\lambda f)^2$.

A further principal feature of the present invention is a layer 26 of a non-linear material in the array 14 at the focal plane. The term non-linear refers to a characteristic of the material, that is, that the amount of light absorbed or reflected in the layer is not a linear function of the amount of light incident on it. Instead, light at a low level of intensity, e.g. non-collimated ambient light, passes through the layer 26 with no significant diminution of its intensity, while extremely intense light, e.q. collimated light brought to a focus on the layer 26, will become highly absorbed or reflected. The opacity or reflectivity of the non-linear material is a function of its resistivity (good conductors are normally reflective and therefore highly opaque). Vanadium dioxide, $VO_2$, is a suitable non-linear material. Its resistivity as a function of its temperature in degrees centigrade is shown in FIG. 7.

Figure 7:
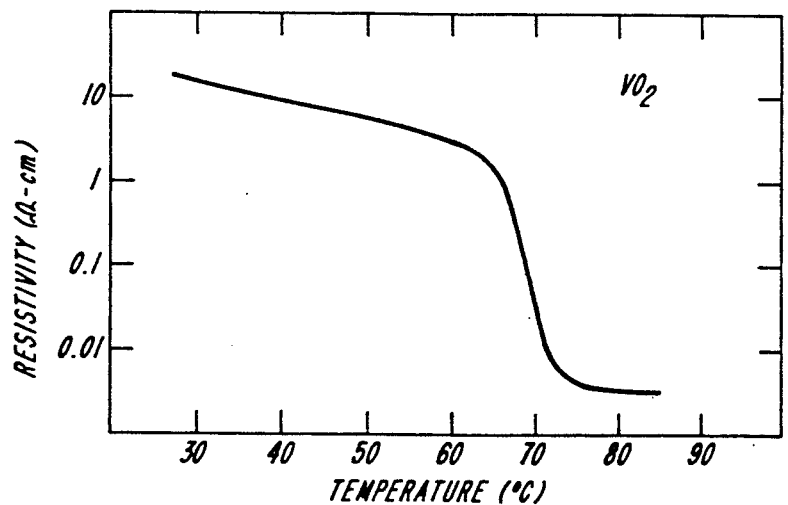
FIG. 7 is a graph of the resistivity of a suitable non-linear material as a function of temperature.

This particular material functions as a non-linear material when positioned at the focal plane of the telescopes 12,12' forming an array or shield 14 because the collimated light brought to a focus on the layer 26 heats, and thereby changes, its resistivity and its opacity, as indicated by FIG. 7. At normal temperatures the layer 26 of $VO_2$ is clear and readily transmits light so that the image of the focal plane will appear to be an infinity to a viewer looking through the telescope with such a layer 26. The heating produced by collimated light causes the non linear material to darken and/or reflect. The layer 26 thus acts as an optical switch or limiter. The thickness of the layer 26 can be adjusted to absorb safely a sufficient percentage of the incident radiation to protect the imaging device while not interfering with normal viewing. While this particular non-linear material functions as a result of heating, as will be readily understood by those skilled in the art, other materials are non-linear and respond optically to other parameters such as the intensity of the incident light, not the temperature of the material.

Stated broadly, the invention utilizes a set of optical surfaces and a non linear material organized as an optical cell which performs three functions. One or more surfaces brings collimated light to at least one focus internal to the cell. At this at least one focus, the non linear material acts as an optical limiter, by any of a variety of possible mechanisms, including a heating of the material to increase its opacity and/or reflectivity. Finally, one or more refracting surfaces causes the light to emerge from the set of optical surfaces parallel to the light entering it. The optical cell re-collimates the light brought to a focus on the non-linear material and inverts the image. The inversion of the image is significant to obtain a coherent wavefront emerging from a mosaic of such cells. As will be discussed in more detail below, the resolution of such a mosaic of optical cells is better than the resolution of an individual cell.

Figure 3:
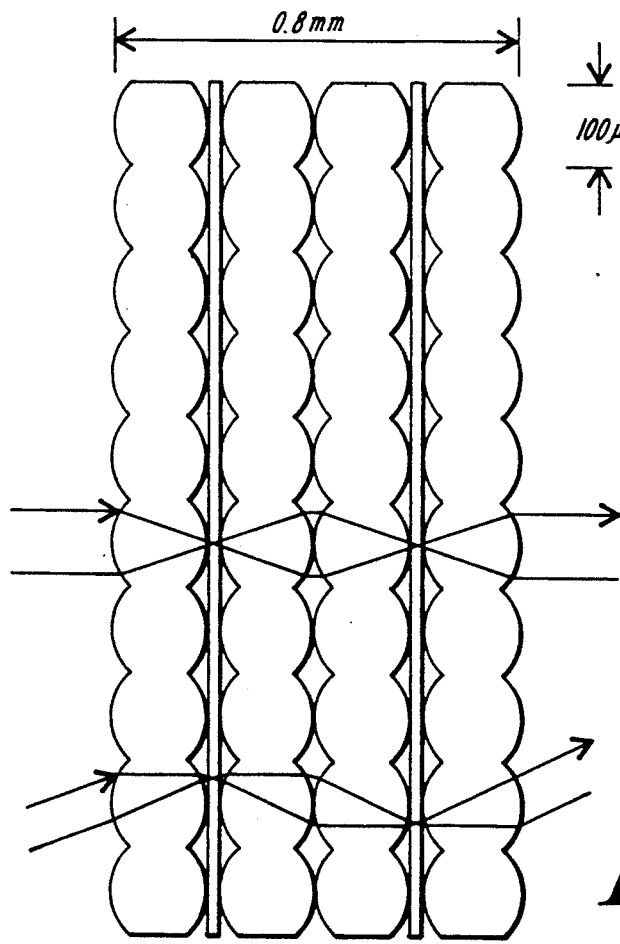
FIG. 3 is a view in vertical section of a portion of an optical shield according to the present invention formed as a mosaic of the cells shown in FIG. 2 and with a layer of non linear absorbing material located at each focal plane.
Figure 4:
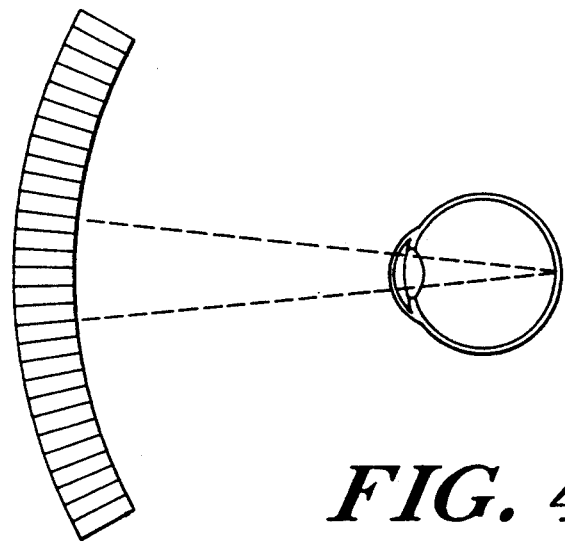
FIG. 4 is a highly simplified view in vertical section of a curved laser shield spaced from an eye.

FIGS. 3 and 4 illustrate arrays or shields 14,14', respectively, of telescopes as shown in FIGS. 1 or 2 formed in a mosaic as a continuous sheet. In the embodiment shown in FIG. 3, the individual telescopes 12,12' are not formed individually, but rather are defined by associated surfaces $S_1$-$S_4$ formed in a material of suitable optical characteristics—e.g. transparency and refractive index and suitable manufacturing characteristics—e.g. readily manufactured by conventional plastic molding techniques. The required shielding gain G is determined, as noted above, by the size of the individual telescopes, which in turn determines the thickness of the array. For example, for the FIG. 3 embodiment, for visible light at $\lambda = 0.5\mu$ and for a shielding gain of 10,000 (the gain of the human eye a few degrees from the fovia), if the telescope is F=2 and D=100$\mu$, the thickness of the array is $4Df=0.8$ mm. With a higher F number, optical aberrations can be reduced at the expense of a thicker shield.

FIG. 4 illustrates a particularly important application, eye glasses. As shown, an array 14 of telescopes with a layer of non-linear material disposed at the focal planes in the array is curved with a center of curvature generally coincident with the center of the associated imaging device 18, here an eye. The optical axis of each telescope 12,12' is then radially aligned with the eye. With such a configuration, the eye automatically looks directly into the telescopes as it moves.

The field of view of the telescopes is determined by peripheral vision of the eye The half angle field of view for each telescope that is needed is given approximately by $$\tan\theta = e/s$$

where e is the distance the pupil of the eye moves when the eye rotates in its socket and S is the distance from the pupil to the array 14. If, for example, e=0.7 cm and S=3 cm, $\theta$ is about 13° for the telescopes 12,12', with F=2, the field of view derived from $\tan\theta = \frac{1}{2}F=0.25$ is $\theta = 14°$. Thus the array can accommodate peripheral vision.

An additional characteristic of the arrays 14 of the present invention is that their resolution is significantly better than one might expect given the diffraction limit of an individual 100$\mu$ aperture $\mu = \theta/D = 0.05$ radian = 17 minutes of arc. This is seventeen times worse than the resolution of human vision. Surprisingly, however, a shield according to this invention is not so limited because, provided the shield is made with sufficient precision, the wavefronts emerging from the individual telescopes (or more generally, optical cells) in the array are coherent with those emerging from adjacent cells.

Diffraction causes a wavelet from each exit aperture $S_4$ to merge with neighboring wavelet in a distance $L=D^2/\lambda$. (Note that this assumes that the telescopes or cells do not invert the image since inversion means that rays entering the system will not remain adjacent upon leaving the system.) The interference between these wavelets produces a plane wave (assuming a point like source). The resolution of the array is thus limited not by the diffraction limit of the individual cells, but by the precision in constructing the array. More specifically, if the optical path lengths through the array for rays is constant for parallel rays to a quarter of a wavelength or less, then the diffraction limit is determined by the full aperture, not that of a single optical cell.

This merging of wavelets also has beneficial effect on the aberrations contributed by the individual elements. For example, consider chromatic aberration. If a lens element has indices of refraction $n_1$ and $n_2$ for two colors at the extreme ends of the visual spectrum, then chromatic aberration will introduce an angular aberration given by $$\Delta\theta = \frac{\delta_n}{n-1} \cdot \frac{1}{2F}$$

where $\delta_n = n_2 - n_1$ and $F = f/D$. For typical optical glasses $\delta_n = 0.01$ and n≈1.5. For an F=2 system, $\Delta\theta = 0.005$. This is comparable to the angular spread that is due to diffraction alone, namely $\lambda/D = 0.5/100 = 0.005$. Therefore wavelets "tilted" due to chromatic aberrations will merge to form one waveform. Since the phrase differences between wavelets will reinforce only in the forward direction, chromatic aberration disappears.

This phenomenon can be viewed as the result that when the wavelets combine, wave optics becomes more important than traditional ray tracing analysis useful for isolated lens systems as in cameras. When the shield is taken as a whole, plane waves entering the shield must leave the shield at the same angle as the entered it since on that scale the shield is relatively thin. In other words, while individual cells can utilize thick lens which can be analyzed using traditional ray tracing, when the array as a whole is considers on a scale much greater than that of any individual element, the shield is a thin lens. Another wave of considering why this should be the case is to consider that at the retina an image fixed averages light over an entire Fresnel zone on the surface of the shield. This zone contains may cells and the wavefront is average. As the variation in phase from cell to cell is small, the elements add coherently.

Figure 5:
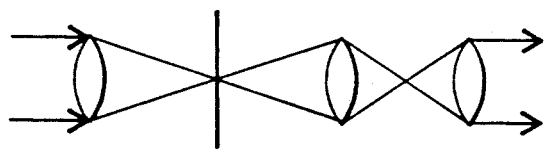
FIG. 5 is view corresponding to FIGS. 1 and 2 showing a three embodiment with one layer of non linear material of the present invention.
Figure 6:
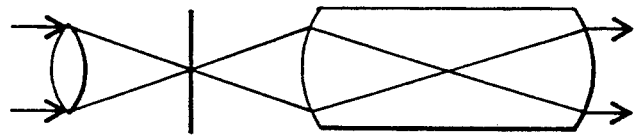
FIG. 6 is a view corresponding to FIGS. 1, 2 and 5 showing a two lens embodiment of the present invention with one thin lens and one thick lens.

FIGS. 5 and 6 show alternative constructions for three and two lens optical cells 12″ and 12‴, respectively also constructed according to the present invention. In the three lens system shown in FIG. 5, a single thin lens 20″ brings collimated light (rays A and B) to a focus on the layer of non-linear layer 26″. A pair of thin lenses 24″, 24″ re-collimate and invert the image at the focal plane. There is a sufficient spacing between the lens 20″ and 24″ to bring the light incident on the entrance aperture to a focus at the non-linear layer. FIG. 6 shows a two lens embodiment similar in construction and operation to the cell shown in FIG. 1 except that the first focusing lens 20‴ is a thin lens and there is again a sufficient spacing between lens elements and the non linear material to produce a focusing of collimated light on the non-linear layer causing it to limit the optical energy it transmits.

While the foregoing discussion has assumed spherical lens elements, it is possible to form one or more lens elements aspherically to correct for aberrations. It is also, of course, possible to use a variety of other well known aberration correcting techniques such as the spacing of elements of different curvatures.

Manufacture can use any of a variety of existing techniques. For example, an individual element can be made with a precision diamond tool and then a step and repeat process can produce a suitable mold for the manufacture of a sheet of one lens elements in side-by side array. The lens can be made thin, using spacers to get the proper distances, or thick, making contact with each other, either directly or with an intermediate layer of a non-linear material.

There has been described an optically-neutral shield that passes ordinary light with no noticeable alteration of the image, but which limits or blocks the transmission of light which is sufficiently collimated (parallel) and of sufficient intensity that when it comes to a focus it is capable of damaging an imaging device such as the human eye. The shield of the present invention has the great advantage over prior art approaches in that its operation is wavelength independent. It can operate as a flat or curved device and therefore lends itself to the formation of many useful articles that require good optical transmission characteristics under ordinary circumstances. The invention also provides a shield with resolution better than would ordinarily be expected from small diameter optical elements that form the device, and which readily corrects for many aberrations. These advantages can be achieved using known materials and manufacturing technology.

While the invention has been described with respect to its preferred embodiments, it will be understood that various modifications and alterations will occur to those skilled in the art. For example, while the optics of the shield have been described with lenses as the principal elements guiding the passage of light through the lens, it is possible to use other mechanisms such as a focusing optical fiber instead of a one power telescope. An array of these fibers becomes a fibre optic bundle with an associated non-linear absorbing layer sandwiched between bundles in the manner shown in FIG. 3. These and other such modifications and variations are intended to fall within the scope of the appended claims.

What is claimed is:

1. An optical device that is optically neutral to normal light but at least partially blocks the transmission through the device along a first direction of collimated light to an imaging device which may include the human eye, comprising
an array of optical cells each having (i) means for bringing collimated light incident on its entrance aperture to at least one internal focus, (ii) means for limiting the transmission of said focused light by at least one of the techniques including attenuation and reflection, and (iii) means for re-collimating and inverting the light after it has been focused and limited,
wherein said optical cells are arrayed to form a mosaic with the precision of the location of the cells within the array being sufficient that the light emerging from each of said cells in said mosaic combines coherently with light from other cells in said mosaic to yield an image with a resolution greater than that obtainable with a single one of said optical cells.

2. The optical device of claim 1 wherein said precision is within one quarter of the wavelength of the light being transmitted through said device.

3. The optical device of claim 1 wherein said mosaic is flat.

4. The optical device of claim 1 wherein said mosaic is curved.

5. The optical device of claim 1 wherein a plurality of associated ones of said first, lens means, said second lens means, and said inverting means are secured in said array with a precision such that the light exiting said second surfaces $S_4$ combines coherently to produce an image with a resolution greater than that obtainable with a single one of said lens means.

6. The optical device of claim 5 wherein said precision of securing is within one quarter of the wavelength of the light being transmitted through said device.

7. The optical device of claim 4 wherein said array is flat.

8. The optical device of claim 4 wherein said array is curved.

9. The optical device of claim 1 wherein said at least one of said first and second lens means are internally optically coupled to adjacent ones of said first and second lens means to provide an enhanced field of view.

10. The optical device of claim 3 wherein said lens elements are made of transparent materials with different indices of refraction to achromatize the device.

* * * * *